United States Patent
Barone et al.

(10) Patent No.: US 9,265,702 B2
(45) Date of Patent: Feb. 23, 2016

(54) COSMETIC POWDER

(71) Applicant: Coty Inc., New York, NY (US)

(72) Inventors: Salvatore J. Barone, Staten Island, NY (US); Louis J. Veltry, Hopatcong, NJ (US)

(73) Assignee: Coty Inc., New York, NY (US)

(*) Notice: Subject to any disclaimer, the term of this patent is extended or adjusted under 35 U.S.C. 154(b) by 0 days.

(21) Appl. No.: 14/428,819

(22) PCT Filed: Feb. 6, 2013

(86) PCT No.: PCT/US2013/024875
§ 371 (c)(1),
(2) Date: Mar. 17, 2015

(87) PCT Pub. No.: WO2014/051660
PCT Pub. Date: Apr. 3, 2014

(65) Prior Publication Data
US 2015/0231044 A1     Aug. 20, 2015

Related U.S. Application Data

(60) Provisional application No. 61/705,319, filed on Sep. 25, 2012.

(51) Int. Cl.
| | |
|---|---|
| A61K 8/58 | (2006.01) |
| A61K 8/894 | (2006.01) |
| A61K 8/49 | (2006.01) |
| A61K 8/02 | (2006.01) |
| A61K 8/362 | (2006.01) |
| A61Q 1/00 | (2006.01) |
| A61K 8/19 | (2006.01) |
| A61K 8/34 | (2006.01) |
| A61Q 1/10 | (2006.01) |
| A61K 8/25 | (2006.01) |

(52) U.S. Cl.
CPC ............... *A61K 8/342* (2013.01); *A61K 8/022* (2013.01); *A61K 8/19* (2013.01); *A61K 8/25* (2013.01); *A61K 8/362* (2013.01); *A61K 8/494* (2013.01); *A61K 8/58* (2013.01); *A61K 8/894* (2013.01); *A61Q 1/10* (2013.01); *A61K 2800/5922* (2013.01); *A61K 2800/805* (2013.01)

(58) Field of Classification Search
CPC ...................................................... A61K 8/922
See application file for complete search history.

(56) References Cited

U.S. PATENT DOCUMENTS 4,756,906 A * 7/1988 Sweeny ............... A61K 8/11
424/63
6,517,628 B1   2/2003 Pfaff et al.

FOREIGN PATENT DOCUMENTS

| EP | 1045014 A2 | 10/2000 |
| WO | WO-2014051660 A1 | 4/2014 |

OTHER PUBLICATIONS

"European Application Serial No. 13704867.4, Office Action mailed Jul. 8, 2015", 2 pgs.
"European Application Serial No. 13704867.4, Response filed Jul. 22, 2015 to Office Action mailed Jul. 8, 2015", 16 pgs.
"International Application Serial No. PCT/US2013/024875, International Preliminary Report on Patentability mailed Apr. 9, 2015", 8 pgs.
"Eye Loose Powder", XP002719462, Database accession No. 1300334, (Mar. 2010).
"Highlight Powder", XP002719463, Database accession No. 846524, (Jan. 2008).
"International Application Serial No. PCT/US2013/024875, International Search Report mailed Mar. 14, 2014", 4 pgs.
"International Application Serial No. PCT/US2013/024875, Written Opinion mailed Mar. 14, 2014", 6 pgs.
"Make-Up Quad", XP002719460, Database accession No. 1278204, (Feb. 2010).
"Platinum Star Powder", XP002719461, Database accession No. 1243783, (Nov. 2009).

* cited by examiner

Primary Examiner — Scott Long
Assistant Examiner — Sarah Alawadi
(74) Attorney, Agent, or Firm — Schwegman Lundberg & Woessner, P.A.

(57) ABSTRACT

What is claimed is: a loose cosmetic powder, comprising: a base component including particles that include one or more of talc, mica, zinc stearate, boron nitride, and one or more pigments; and color bits, wherein the loose cosmetic powder displays a color change when subjected to an application of pressure.

8 Claims, No Drawings

COSMETIC POWDER

RELATED APPLICATION

This application is a U.S. National Stage Filing under 35 U.S.C. §371 of International Patent Application Serial No. PCT/US2013/024875, filed Feb. 6, 2013, and published on Apr. 3, 2014, as WO 2014/051660 A1, which claims the priority of U.S. provisional application, Ser. No. 61/705,319, filed Sep. 25, 2012, which are incorporated herein by reference in their entirety.

FIELD

Inventive subject matter disclosed herein relates to color changing cosmetic powder composition embodiments and method embodiments for using color changing cosmetic powder composition embodiments.

BACKGROUND

Women have been employing skin foundations to achieve a lightening effect since at least Greek and Roman times. Ancient Greek women used white lead powder and chalk to lighten facial features. Ancient Greek women also applied crushed mulberries or red beet liquid to their cheeks as a blush or rouge. Ancient Egyptian and Indian women accentuated their eyes with kohl, which was made of burnt almonds, crushed antimony, copper, ash, ochre, malachite and chryscolla. Ancient Greek women employed powders from lapis lazuli and malachite to accentuate their eyes.

The first modern, commercially successful foundation powder was PAN CAKE, developed by Max Factor in the 1930's. This powder used talc and was applied to skin with a wet sponge.

SUMMARY

Embodiments disclosed herein relate to a loose cosmetic powder. The powder includes a base comprising particles that include one or more of talc, mica, zinc stearate, boron nitride, and one or more pigments. The powder also includes color bits. The powder also includes an oil phase effective for impregnating particles of the base and color bits, wherein the loose cosmetic powder displays a color change when subjected to an application of pressure.

Embodiments also include a method for sculpting color on skin above a user's eye. The method includes applying a loose powder embodiment, disclosed herein, to the skin, above a user's eye to cover an area of skin. The loose powder is applied with a force effective to change the color of the loose powder over at least a portion of the area of skin.

Another embodiment includes a method for making a loose cosmetic powder effective for displaying a color change when subjected to an application of pressure. The method includes mixing particles of one or more of talc, mica, zinc stearate, boron nitride, and pigments, to make a loose powder. The method also includes adding a color bit to the loose powder. The color bit is added in a concentration effective for the loose powder and color bit to display a color change when subjected to an application of pressure.

One other embodiment includes a loose cosmetic powder. The loose cosmetic powder includes a base component comprising particles that include one or more of talc, mica, zinc stearate, boron nitride, and one or more pigments. The loose cosmetic powder also includes color bits; wherein the loose cosmetic powder with color bits displays a color change when subjected to an application of pressure.

DETAILED DESCRIPTION

The following detailed description includes references to embodiments, which are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the inventive subject matter is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Color changing cosmetic powder composition embodiments disclosed herein include loose powder embodiments that are partially pigmented. Dispersed within the powder embodiments are small bits of a solid colorant that has been at least partially covered by surrounding ingredients, thereby becoming camouflaged. In one embodiment, the color bits are Coloreze BKIO Powder Bits, manufactured by IFC Solutions. The color bits, in one embodiment, include red iron oxide, black iron oxide and yellow iron oxide, ferric ferrocyanide, and FD&C Yellow No. 5 Aluminum Lake.

The color changing cosmetic powder displays a color change when subjected to an action, such as a pressing or movement, when applied to skin. The pressing or movement, whether performed with an implement or a finger of a user, differentially applies a pressure over a surface of skin, such as skin above the user's eye. This differential pressure produces a sculpting effect of single color gradation or intensity or brightness for some embodiments and color transformations for other embodiments. The concentration of color bits in the powder embodiments that produce the color changing effect is at 5% to 30% by weight of the color change composition.

In one embodiment, the color bits are blue. The powder surrounding the color bits is green. Upon application to skin above the eye, the color is green. Upon pressing the powder, once it is applied to skin, the blue color is exposed. With blending, a yellow color appears.

The loose powder embodiments that include the color bits are applicable to the skin, face, eyelid, or body with either finger tips or a suitable applicator. While applying, a user can exert an extra application pressure by pressing a finger or implement, sufficient to cause the color bits to become exposed and to impart a second color that had been camouflaged by the powder. For other embodiments, the color bit is a more intense color than the powder. Pressing the formulation once it is applied to the skin exposes a more intense bit color that had been camouflaged. Additionally, movement of the powder and color bits clears at least part of the surface of the color bits and removes the camouflage of the color bits. This application of pressure allows the user to adjust her shade to a desired intensity or to actually sculpt the color as an artist would while painting a canvas. With an application of pressure, users can change the coloring of loose powder color from light to dark, pale frost to intense color and everything in between, upon application to skin.

The Composition

The color changing loose powder with color bits includes a base make up component that includes particles of talc, mica, zinc stearate, boron nitride, and pigments. For some embodiments, other textural enhancers are added, such as polymethylmethacrylate, nylon, silica, HDI/Trimethylol Hexyl lactone, surface treated powders, and other materials known in the art, to impart a desired sensorial result. Presented herein are specific examples of color change powder formulations. These formulations are presented as exemplary embodiments only and are not intended to limit the inventive embodiments disclosed herein.

One color change powder formulation is as follows:

| Constituent | INCI Name | Wt. %(1) |
|---|---|---|
| Talc | talc | 17.4 |
| Mica LL ST1409 | Mica, lauroyl lysine | 15.0 |
| Zinc Stearate | Zinc stearate | 2.0 |
| Boron Nitride | Boron nitride | 0.7 |
| Coloreze BKIO Powder Bits | | 30.0 |

Timica Extra

| Large Sparkle | mica, titanium Oxide | 12.0 |
|---|---|---|
| SP Silver White | mica, titanium Dioxide | 8.0 |
| Oil Phase | various cosmetic Oils | 14.9 |

Concentrations of the powder bits in the color change powder are, for some embodiments, at least 30% by weight. Concentration of the color bits is 10% to 30% by weight. The color bits are Coloreze BKIO Powder Bits and are obtained from International Foodcraft Corporation of Linden N.J.

The color change powder is formulated by combining the powders of talc and mica and then adding the oil phase to make the base. For some embodiments, cosmetic pearls are also incorporated into the base for imparting shine and glittery effects into the loose powder.

Coloreze BKIO Color bits are added to loose powder base embodiments and are processed under moderate shear mixing for a short period of time.

Another color change powder composition is as follows:

| Constituent | INCI Name | Wt. % |
|---|---|---|
| Talc | talc | 31.1 |
| Mica LL ST1409 | Mica, lauroyl lysine | 15.0 |
| Zinc Stearate | Zinc stearate | 2.0 |
| Boron Nitride | Boron nitride | 0.7 |
| C47-060 | Titanium dioxide | 1.8 |
| C33-1700 | Iron oxides | 4.0 |
| C69-002 | FD&C Yellow No. 5 | 0.5 |
| Coloreze IB Powder Bits | | 10.0 |
| Colorona MP-25 | | 20.0 |
| Oil Phase | Various cosmetic oils | 14.9 |

An oil phase composition is prepared by mixing oil constituents together separately. The oil phase composition includes a carefully selected combination of materials having a multi functional capacity. One oil phase embodiment includes Lexfeel 21 in a concentration of 4.5%, Abil Wax 9801 in a concentration of 3%, Jarcol I-18CG in a concentration of 6.3%, Euxyl PE 9010 in a concentration of 0.9%, Hexaglyn PR-15 in a concentration of 0.2% by weight of the color change composition.

The oil phase composition acts to "wet out" the powders and pigments in the color change powder composition. The oil phase also provides lubricious application, and aids in the adherence of the product to skin such as that on the eye lid. By "wet out" is meant that the oil phase impregnates the structure of powder particles and color bits. The oil phase composition thus conditions and softens the color bits. The oil phase composition is heated to 60 degrees Centigrade prior to addition to the batch of loose powder and color bits to enhance the wetting and softening effects. The range of temperature is 55° C. to 70° C. The batch is then mixed with low shear to distribute the oil evenly while coating and conditioning the color bits. Careful attention is taken not to damage or over process the color bits.

The Application

The color changing cosmetic powder embodiments are applicable with a brush, sponge tip applicator or by using fingertips. The loose powder embodiments are spread over the eyelid yielding generally the shade of the bulk powder tone with the pearlescent pearls highlighting the eyelid. By applying additional pressure, a user can either deepen the shade or transform it into a different color, depending upon colors present in the color bits. For some embodiments, deepening color occurs in shades ranging from a grey to black, light blue to dark blue, or pink to red, and other color changes. Transforming shade possibilities include yellow to green, peach to brown, white to red, and pink to blue. By using a technique of selective pressing, the user can sculpt the areas around the eye to create different color and intensity schemes.

Color Bits

The color bits component of the color changing cosmetic powder produces the sculpting and transitioning effects of the color changing cosmetic powder, when it is subjected to pressure as described herein. The color bits include one or more pigments, such as iron oxides, ferric and ultramarine blue, manganese violet, and or organic colorants such as FD&C Yellow #5, D&C Red #7 just to name conventional pigments. For one embodiment, the color bits are Coloreze BKIO Powder Bits obtained from IFC Solutions.

When added to the powder bulk, the color bits are processed with low energy in order to mix the color bits into the powder and prevent particle break down. This low energy processing is followed by the addition of the oil phase that has been heated to 60° C. Continued low energy mixing distributes the oil which conditions, i.e. softens, the color bits. The result is a smooth powder that, when pressed against the eye lid, cheeks, or face that releases the color in a color release, a shade of color intensifies for some embodiments, or changes to a different color for other embodiments and intensifies and or changes the shade of the eye shadow. The color blends with the powder composition.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description

What is claimed is:

1. A loose cosmetic powder, comprising:
   a base component comprising particles that include one or more of talc, mica, zinc stearate, boron nitrate, and one or more pigments, the base component having a first color;
   color powder comprising particles of solid colorant in a concentration of 5%-30% by weight of the loose cosmetic powder, the color powder comprising particles that include one or more of red iron oxide, black iron oxide, yellow iron oxide, ferric ferrocyanide, and Yellow No. 5 aluminum Lake, having a second color, the color powder particles at least partially coated by base; and
   an oil phase in a concentration of 15% comprising trimethylolpropane tricaprylate/tricaprate (Lexfeel 21) in a concentration of 4.5%, cetyl dimethicone (Abil Wax 9801) in a concentration of 3%, isostearyl alcohol (Jarcol 1-18CG) in a concentration of 6.3%, by weight of the loose cosmetic powder, that impregnates particles of the base and color powder, wherein the loose cosmetic powder displays a color change when subjected to application of pressure.

2. The loose powder of claim 1, wherein the cosmetic powder displays one color prior to application of pressure and a second color after application of pressure.

3. The loose powder of claim 1, wherein the cosmetic powder displays one color prior to application of pressure and a highlighted color after application of pressure.

4. The loose powder of claim 1, wherein the color powder particles release pigment upon exposure to pressure from a user's finger or an appliance.

5. The loose powder of claim 1, wherein the color powder particles retain pigment in the absence of an application of pressure from a user.

6. The loose powder of claim 1, wherein the color powder further comprise cosmetic pearls.

7. A method of sculpting color on skin above a user's eye, the method comprising:
   applying the loose powder of claim 1 on the skin above a user's eye to cover an area of skin; and
   applying force effective to change the color of the loose powder over at least a portion of the area of skin.

8. A method for making loose cosmetic powder effective for displaying a color change when subjected to an application of pressure, the method comprising:
   mixing particles of a base component comprising particles that include one or more of talc, mica, zinc stearate, boron nitride, and one or more pigments, the base component having a first color;
   adding color powder particles of solid colorant to the base component to make a loose cosmetic powder in a concentration of 5% to 30% by weight of the loose cosmetic powder, the color powder particles comprising one or more particles of red iron oxide, black iron oxide, yellow iron oxide, ferric ferrocyanide, Yellow No. 5 Aluminum Lake, the color powder particles having a second color wherein the color powder particles are at least partially coated by the base;
   and adding an oil phase in a concentration of 15% comprising trimethylolpropane tricaprylate/tricaprate (Lexfeel 21) in a concentration of 4.5%, cetyl dimethicone (Abil Wax 9801) in a concentration of 3%, isostearyl alcohol (Jarcol 1-18CG) in a concentration of 6.3%, by weight of the loose cosmetic powder, that impregnates particles of the base and color powder, wherein the loose cosmetic powder displays a color change when subjected to an application of pressure.

* * * * *